Nov. 12, 1963 G. MERRILL Plant Pat. 2,295
PEACH TREE
Filed Dec. 4, 1961
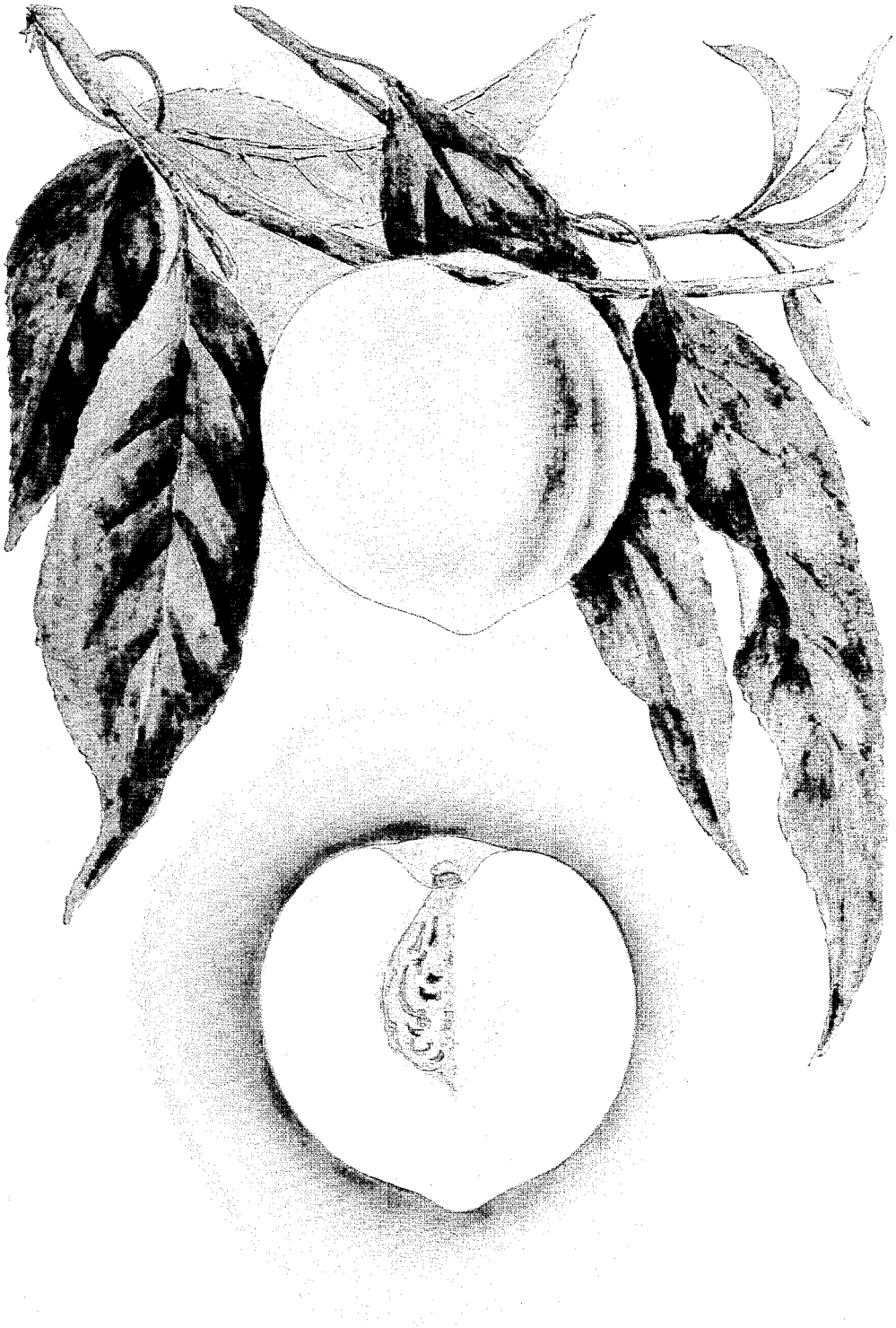
WITNESS
Addison E. Avery
INVENTOR GRANT MERRILL
HUEBNER & WORREL
BY Richard M. Worrel
ATTYS United States Patent Office Plant Pat. 2,295
Patented Nov. 12, 1963

2,295
PEACH TREE

Grant Merrill, P.O. Box 392, Red Bluff, Calif.

Filed Dec. 4, 1961, Ser. No. 157,026
1 Claim. (Cl. Plt.—43)

The present invention relates to a peach tree and more particularly to a new and distinct variety thereof broadly characterized by being a tree which has a very late bloom and, within a short ripening season, bears large, yellow-fleshed, freestone peaches having a skin of an intensely red color.

A distinctive characteristic of the present variety is its ripening date which, in California, is about that of the Redhaven (unpatented) peach tree or about thirty days earlier than the Elberta (unpatented) peach tree. Furthermore, the fruit has a slightly raised suture and a skin of a rich, red color. In comparison with Merricle P–75 peach tree of United States Plant Patent No. 1,872, which it most nearly resembles, the instant variety ripens at about the same time, but is more productive, has larger and more vigorous leaves, and produces larger and firmer fruit, which is distinctly more intensely red in color.

Because of the rich soil and favorable climatic environment prevailing in most of the commercial peach farming areas of California, the peach trees tend to produce rank growth and dense shade resulting in serious impairment of the coloring of the fruit. Inasmuch as most fruits rely on eye appeal for their sales, color impairment is highly undesirable. A primary object of the plant breeding procedures which resulted in the development of this new peach variety was to achieve a highly colored red peach fruit which attains its high color and firmness even under conditions of rank growth and dense shade.

Further objects and advantages will become more fully apparent in the subsequent description in the specification.

I originated the present variety of peach tree on my farm near Red Bluff, Tehama County, California in the following manner: Seeds from a J. H. Hale (unpatented) peach tree growing next to an experimental orchard were planted, and a selection of the resulting seedlings were grown to maturity. This process of planting seeds from open pollinated blossoms continued for four generations, each time selection being made for high color, firmness and good shipping qualities. In the fourth generation, the selection of the subject variety peach tree was made. In the fall of 1956, several trees planted the previous year were budded to this selection on my farm at Red Bluff, Tehama County, California, and the trees fruited in July 1958. The fruit and tree characteristics proved identical to those of the original fourth generation selection.

The accompanying drawing is a water color painting of a characteristic twig of the subject peach tree bearing foliage and a mature fruit and additionally, showing a fruit of the subject variety divided on its suture plane to reveal flesh coloration and pit characteristics.

Referring now more specifically to the pomological details of this new and distinct variety of peach tree, the following has been observed under the ecological conditions prevailing at my farm near Red Bluff, Tehama County, California and is an outline description thereof. All major color plate identifications are by reference to Maerz and Paul Dictionary of Color.

*Tree*

Size: Large, vigorous, medium upright, medium dense, vase formed by pruning, productive, regular bearer.
Trunk: Medium stocky, medium smooth.
Branches: Lenticels, medium in quantity, medium sized.
Leaves: (Selected from midportion of vigorous unbranched terminal shoot 18" to 24" long.)

*Size.*—Large.
*Length.*—6¼" to 8½", average 7".
*Width.*—1 5/16" to 1 9/16", average 1⅜".
*Form.*—Lanceolate, tip acuminate, medium thick.
*Color.*—Upper surface, medium green (22–L–7); underside has a slight yellow tinge (22–K–6). Heavy midrib, lighter green (17–K–1).
*Class* (Meader and Blade: Proceedings of Am. Soc. Hor. Sc., vol. 37, page 206).—Mostly 2, some 3. Width-length ratio—.20. Apex angle (1" from tip) 25° to 27°, average 26°. Base angle (½" from petiole) 60° to 80°, average 75°.
*Margin.*—Glandular, crenate.
*Petiole.*—Medium long, medium thick.
*Stipules.*—At base of leaf, falling off early.
*Glands.*—0 to 5, average 4. Medium size, reniform, green to greenish yellow, few show red, at base of leaf and on petiole.

Flower buds: Medium size, medium length, truncate to obtuse, plump, free, pubescent.
Flowers: Late as compared with Redhaven (unpatented) averaging five days later over a four year period, small, pink. Pollen—moderately abundant.

*Fruit*

Maturity when described, soft ripe.
Size: Variable.
*Axial diameter.*—2½" to 3", average 2 13/16".
*Transverse in suture plane.*—2¾" to 3", average 2⅞".
*At right angles to suture plane.*—2⅝" to 2⅞", average 2 11/16".
Form: Variable, globose to some slightly obovate.
*Suture.*—Distinct, raised, has slight depression beyond pistil point.
*Lips.*—Unequal to pronounced on some fruits.
*Ventral surface.*—Rounded.
*Cavity.*—Flaring, abrupt, elongated in suture plane, suture showing on both sides. Depth, 7/16" to ⅝", average ½". Breadth ⅜" to ½", average 7/16". Markings yellow to yellowish green, red blush extending in some.
*Base.*—Truncate.
*Apex.*—Mostly mucronate, few cuspidate.
*Pistil point.*—Apical.
*Stem.*—Short, length ⅜", diameter ⅛".
Skin: Medium thick, medium tender, tenacious to flesh when firm ripe, free when soft ripe, no tendency to crack.
*Color.*—Under color, yellow (9–G–7) to orange yellow (11–L–11). Red blush over most of the area, (2–K–9) to (2–L–11).
*Down.*—Scant, short, rolls up when rubbed.
Flesh:
*Color.*—Various shades of yellow throughout with almost no red except next to pit cavity. Yellow runs from (9–L–4) to (9–L–7).
*Surface of pit cavity.*—Yellow with considerable red.
*Amygdalin.*—Scant.
*Juice.*—Moderate, rich.
*Texture.*—Firm and fine.
*Fibers.*—Few and fine.
*Ripens.*—Evenly.
*Flavor.*—Subacid, mild and delicate.
*Aroma.*—Mild.
*Eating quality.*—Good.
Stone: Free, adheres to flesh along ventral edge near base on some, with short fibers when soft ripe, retains short fibers, like threads along ridge on some.
*Size.*—Medium.
*Length.*—1⅜" to 1⅝", average 1 15/32".
*Breadth.*—⅞" to 1⅛", average 1 1/16".

*Thickness.*—11/16" to 13/16", average ¾".
*Form.*—Usually long, obovate.
*Base.*—Slightly oblique.
*Hilum.*—Oval.
*Apex.*—Cuspidate.
*Sides.*—Varied, equal to unequal, frequently flattened on the one side.
*Surface.*—Irregularly furrowed and pitted.
*Pits.*—Ovate to ovoid.
*Ventral edge.*—Thick with many small grooves in the center and one large groove on either side.
*Dorsal edge.*—Two ridges with deep furrows in-between, discontinuous to nearly so at the apex.
*Color.*—Tan (5–A–12).
*Tendency to split.*—Little.

Use: Fresh market local or distant, suitable for drying or canning.

Keeping quality: Good.

Although the new variety of peach tree possesses the described characteristics under the growing conditions prevailing throughout most of the commercial peach producing areas of California, having been first observed near Red Bluff, Tehama County, California and the northern end of the Sacramento Valley and later confirmed by observation of the same variety near the southern end of the San Joaquin Valley of California, approximately four hundred miles farther south, it is to be understood that variations of the usual magnitude in characteristics incident to growing conditions, fertilization, pruning, thinning and pest control are to be expected.

Having thus described and illustrated my new variety of peach tree, what is claimed as new and desired to be secured by Letters Patent is:

A new and distinct variety of peach tree substantially as illustrated and described and which is characterized by its late bloom averaging five days later than the Redhaven (unpatented) peach tree; its bearing within a short ripening season of large, yellow-fleshed, freestone fruit having a slightly raised suture and a skin of a rich, red color, the fruit ripening about with Redhaven peach tree but approximately thirty days ahead of Elberta (unpatented); and in its most nearly resembling Merricle peach tree of United States Plant Patent No. 1,872, ripening at about the same time, but being distinguished therefrom in its greater vigor and productivity and in its bearing of larger, firmer fruit having a skin more distinctively intensely red in color.

No references cited.